United States Patent [19]

Schlaefer

[11] 3,933,888
[45] Jan. 20, 1976

[54] PRODUCTION OF UNSATURATED ACIDS, ESTERS AND NITRILES, AND CATALYST THEREFOR

[75] Inventor: Francis W. Schlaefer, Pennsauken, N.J.

[73] Assignee: Rohm and Haas Company, Philadelphia, Pa.

[22] Filed: Oct. 6, 1972

[21] Appl. No.: 295,743

[52] U.S. Cl......... 260/465.9; 260/405.5; 260/486 R; 260/526 N; 252/426; 252/438
[51] Int. Cl.² .............. C07C 120/00; C07C 69/52; C07C 69/54; C07C 57/02
[58] Field of Search........... 260/465.9, 486 R, 526 N

[56] References Cited
UNITED STATES PATENTS

| | | |
|---|---|---|
| 3,247,248 | 4/1966 | Sims et al. ............................ 260/526 |
| 3,535,371 | 10/1970 | Wolf et al. ............................ 260/486 |
| 3,574,703 | 4/1971 | Hagemeyer, Jr. et al......... 260/465.9 |
| 3,578,702 | 5/1971 | Snapp, Jr. et al.................... 260/486 |
| 3,840,587 | 10/1974 | Pearson ........................... 260/486 D |

*Primary Examiner*—Joseph Paul Brust

[57] ABSTRACT

Alkanoic acids, esters of such acids, and alkyl nitriles are reacted with formaldehyde in the presence of a basic catalyst comprising pyrogenic silica to form $\alpha,\beta$-unsaturated acids, the esters of such unsaturated acids or $\alpha,\beta$-unsaturated nitriles. The pyrogenic silica is especially effective when treated with activating agents which provide basic sites on the pyrogenic silica catalyst support, such as organic bases, inorganic bases of Groups IIA and IIIA metals, and precursors of such bases.

12 Claims, No Drawings

PRODUCTION OF UNSATURATED ACIDS, ESTERS AND NITRILES, AND CATALYST THEREFOR

This invention relates to a process for the production of $\alpha,\beta$-unsaturated acids, the esters of such acids, $\alpha,\beta$-unsaturated nitriles, and to a novel catalyst used in such process. More particularly, this invention relates to a method for the reaction of alkanoic acids, esters of such acids, and alkyl nitriles with formaldehyde and a novel catalyst system for use in such reactions.

Unsaturated acids, such as methacrylic and acrylic acids, acrylonitrile, and the esters of such acids, such as methyl methacrylate, are widely employed for the production of corresponding polymers, resins and the like. Various processes and catalysts have been proposed for the conversion of alkanoic acids, such as propionic acid, and formaldehyde to the corresponding unsaturated monocarboxylic acid, e.g. methacrylic acid. Generally, the reaction of the acid and formaldehyde takes place in the vapor or gas phase while in the presence of a basic catalyst.

Various catalysts have been proposed for such reaction. For example, U.S. Pat. No. 3,247,248 describes a process for the reaction of formaldehyde and acetic acid or propionic acid in the presence of a natural or synthetic aluminosilicate catalyst that may include alkali or alkaline earth metals, such as the aluminosilicates of sodium, potassium rubudium, magnesium, calcium, strontium or barium. In addition, the use of silica gel in combination with an alkali metal or alkaline earth metal hydroxide as a catalyst for this reaction is described. Similarly, U.S. Pat. No. 3,051,747 describes the preparation of acrylic acids by reacting an alkanoic acid and formaldehyde in the presence of a catalyst comprising an alkali metal salt of the alkanoic acid supported on alumina. Similar teachings are found in an article by Vitcha et al entitled "Vapor Phase Aldol Reaction"; "I & EC Product Research and Development," Vol. 5, No. 1, (March 1966) at pages 50-53, wherein the vapor phase reaction of acetic acid and formaldehyde is described employing catalysts comprising alkali and alkaline earth metal aluminosilicates, silica gel, alumina and the like.

It has now been found that alkanoic acids, their esters, and alkyl nitriles may be reacted with formaldehyde in the presence of a novel catalyst that is capable of providing greater conversions, yields and accountabilities than are provided with the catalysts of the prior art. In accordance with the present invention, alkanoic acids, esters thereof, and alkyl nitriles are reacted with formaldehyde in the presence of a basic catalyst comprising pyrogenic silica. Thus, for example, alkanoic acids containing between two and nine carbon atoms, e.g., propionic acid, are reacted with formaldehyde in the presence of a basic catalyst comprising pyrogenic silica to provide unsaturated monocarboxylic acids, e.g., methacrylic acid. Likewise, the esters of such alkanoic acids, e.g., methyl propionate, may be reacted in the presence of a pyrogenic silica catalyst to provide esters of such unsaturated acids, e.g., methyl methacrylate. Moreover, alkyl nitriles, such as acrylonitrile, may be reacted with formaldehyde in the presence of such basic catalyst to provide the corresponding unsaturated nitrile, i.e., acrylonitrile.

The fumed or pyrogenic silicas display radically different properties from silica gel. For example, pyrogenic silica is characterized by its lack of internal porosity, small diameter and the agglomeration of its composite particles. The surface area of pyrogenic silica is almost totally external, and thereby provides a readily available catalytic surface, whereas the surface area of silica gel is substantially internal and therefore less readily available.

In addition to providing increased conversion, yield and accountability, less carbonaceous material is deposited on the pyrogenic silica catalyst of the present invention as compared with prior art catalysts. Accordingly, less frequent catalyst regeneration is necessitated. In addition, by virtue of the open and readily available structure of the pyrogenic silica, a more controlled and even burn-off is experienced during the oxidative regenerative of the catalyst. Thus, catalyst deactivation may be minimized.

Any suitable pyrogenic silica may be employed in the process of the present invention. Commercially available pyrogenic silica generally contains over 99.8 percent silica (as $SiO_2$ on a moisture-free basis). Accordingly, only a minimum of impurities such as aluminum, titanium and iron are present in such commercially available pyrogenic silica. The presence of such impurities in large quantities is undesirable and, generally, it is desirable to employ pyrogenic silica containing no more than about 10 percent of such impurities.

The total surface area of the pyrogenic silica of the present invention is suitably, for example, in the range between about 40 and about 500 square meters per gram, preferably, between about 100 and about 400 square meters per gram. An especially preferred total surface area for the pyrogenic silica is between about 150 and about 300 square meters per gram. A significant characteristic of the pyrogenic silica is its total porosity, which as will be hereinafter demonstrated, is much greater than that of the prior art supports, such as silica gel and the aluminosilicates. Thus, the pyrogenic silica of the present invention suitably has a total porosity volume in the range of between about 3 and about 15 cubic centimeters (cc.) per gram, preferably between about 5 and about 11 cc. per gram. An especially preferred range is between about 6 and about 10 cc. per gram.

The pore size distribution of the total porosity of the pyrogenic silica of the present invention may vary over a broad range. For example, the macropores, (i.e., pores having a diameter in excess of 100,000 A. and the submacropores (i.e., those between 100,000 and 10,000 A.) content should total at least 50 percent. Likewise, less than 30 percent of the pyrogenic silica and preferably less than 25 percent thereof comprises micropores, i.e., pores having an average diameter of less than 1,000 A. An especially preferred range for such micropores is less than about 20 percent. The balance of the pyrogenic silica comprises medium sized pores in the range of between about 10,000 and about 1,000 A. in diameter.

The preparation of pyrogenic silica is described, for example in U.S. Pat. Nos. 2,871,140; 2,876,119; 2,882,254; 2,892,730; 2,898,391; 2,951,044; 2,990,249; 3,006,738; 3,033,801; 3,083,115; 3,086,851; and 3,103,495.

As previously indicated, the process of the present invention comprises the reaction of formaldehyde with an alkanoic acid, an ester of such alkanoic acid, or an alkyl nitrile. Suitable alkanoic acids include those having an $\alpha$-hydrogen, i.e., a hydrogen atom that is alpha to the carboxyl group of the acid. Suitable alkanoic acids include, for example, alkanoic acids containing from about two to about nine carbon atoms, preferably between about two and about five carbon atoms. Thus, suitable alkanoic acids include acetic acid, propionic acid, butyric acid, isovaleric acid, caproic acid, enanthic acid, caprylic acid, pelargonic acid and the like. An especially preferred alkanoic acid for the purposes of the present invention is propionic acid, which reacts with formaldehyde to produce methacrylic acid. Similarly, esters of the foregoing acids may be reacted with formaldehyde in order to provide the corresponding unsaturated ester. Thus, the methyl, ethyl, propyl, butyl, etc. esters of the foregoing acids will react with formaldehyde in the same manner as does the alkanoic acid to provide the corresponding ester of the unsaturated acid. Thus, suitable esters may contain, for example, three to 14 carbon atoms per molecule. Thus, methyl propionate will react with formaldehyde to form methyl methacrylate. Moreover, alkyl nitriles having, for example, from about two to about nine carbon atoms per molecule, preferably, from about two to about five carbon atoms per molecule, such as acetonitrile, propionitrile, butyronitrile, etc., may be reacted with formaldehyde to provide the corresponding unsaturated nitrile, e.g., acrylonitrile. A preferred alkyl nitrile is propionitrile.

The reaction of the acids, esters and nitriles with formaldehyde is a base-catalyzed reaction. Accordingly, if desired, the pyrogenic silica may be employed as the sole catalytic material as it does possess basic sites. Likewise, the pyrogenic silica may be treated with any suitable material that will provide basic sites on the catalyst. Preferably, pyrogenic silica is treated prior to use with an activating material which, upon calcination, will yield basic sites on the pyrogenic silica. Suitable activating agents include, for example, compounds having a pH of between 3 and 14 when the pH measurement is performed on a 0.3 molar solution. Since the treatment of a pyrogenic silica with the activating agent must yield basic sites upon the silica, the activating agent must be a basic material or a material capable of being converted, upon calcination, into a basic material, viz., a base precursor. Thus, while activating agents, such as potassium oxalate and sodium acetate have a pH of about 3 or 4 in a 0.3 molar solution, and thus do not provide a basic pH, pyrogenic silica may be treated with such materials thereafter calcined whereupon basic sites are provided on the pyrogenic silica. Therefore, such activating agents are apparently "base precursors" and are converted upon calcination to a basic form. Suitable activating agents include, for example, an organic or an inorganic basic compound. Thus, for example, the pyrogenic silica may be treated in any suitable manner with a nitrogen-containing organic base, such as ammonia, pyridine, the substituted pyridines, the various alkyl amines, e.g., methylamine, or the like in order to increase the basicity of the pyrogenic silica catalyst. Likewise, the pyrogenic silica may be treated with high molecular weight amine hydrochloride activating agents, such as the benzyl trialkyl ammonium hydrochlorides, wherein the benzyl ring may be unsubstituted or may be substituted by one or two alkyl groups, each substituted alkyl group containing from one to 12 carbon atoms per molecule. The N-substituted alkyl groups may contain, for example, from one to 16 carbon atoms per molecule, and may include substituted alkyl groups. Examples of such compounds include Diisobutyl phenoxy ethoxy ethyl dimethyl, benzyl ammonium chloride, monohydrate;
Diisobutyl cresoxy ethoxy ethyl dimethyl benzyl ammonium chloride, monohydrate;
Methyl dodexyl benzyl trimethyl ammonium chloride;
Methyl dodexyl xylylene bis(trimethyl ammonium chloride);
N-dodecyl dimethyl benzyl ammonium chloride;
N-tetradecyl dimethyl benzyl ammonium chloride;
N-hexodecyl dimethyl benzyl ammonium chloride; or the like.

Upon calcination of the pyrogenic silica that has been treated with such high molecular weight amine, hydrogen chloride is driven off and the amine remains, thereby providing basic sites to the pyrogenic silica.

Moreover, the pyrogenic silica may be treated with an activating agent comprising a sulfur-containing organic base, such as trimethyl sulfonium hydroxide.

The preferred group of basic materials are the inorganic bases, such as metals of Groups IA, IIA and IIIB, including the alkali and alkaline earth metals including sodium, potassium, rubidium, magnesium, calcium, strontium, barium, cesium and the like which may be employed. Likewise, the hydroxides, oxides, superoxides, amides and salts of such metals which decompose below 450°C. may be employed. Thus, basic materials such as scandium hydroxide, scandium oxide, rubidium hydroxide, lanthanum oxide, barium hydroxide, lanthanum hydroxide, cerium oxide, lithium hydroxide, and the like may be employed. Likewise, other bases and base precursors may be employed as activating atents, to treat the pyrogenic silica. Thus, $Sb_2O_3$, $Bi_2O_3$, $Na_2B_4O_7 \cdot 10H_2O$, $Na_3PO_4$, $Na_2CO_3$, $H_3BO_3$—$Na_2B_4O_7 \cdot 10H_2O_3$, $Na_2HPO_4$, $Fe(OH)_2$, $KOCH_3$, $K_2C_4H_4O_6 \cdot \frac{1}{2}H_2O$, $Na_2SiO_3$, $Na_4SiO_4$, $C_2H_3CO_2Na$, $Na_2WO_4 \cdot 2H_2O$, $La_2O_3$, $Cs_2MoO_4$, $SnO_2$, $MgAlSiO_4$, and the like, may be suitably utilized.

The preferred inorganic bases include the Group IA and IIA bases, such as sodium hydroxide, potassium hydroxide, cesium hydroxide, calcium carbonate, calcium hydroxide, sodium oxalate, sodium amide, cesium silicate and the like. The alkaline metal hydroxides, such as potassium and cesium hydroxide are especially preferred.

The activating agent may be provided to the pyrogenic silica in any suitable manner. Thus, for example, a base, such as aqueous potassium hydroxide, may be slurried with the pyrogenic silica, heated and agitated to form a paste which may be dried and calcined to form the resultant catalyst. In this manner the added base is mulled with the finely divided silica. Any suitable calcining conditions may be utilized. Thus, for example, calcining temperatures in the range of between about 330° and about 460°C. may be employed. Preferably, lower temperatures are utilized, e.g., between about 340° and 385°C., as higher temperatures may reduce the surface area of the catalyst and hence result in lower conversions. Calcination may be conducted in any suitable atmosphere, e.g., nitrogen, air, or the like.

Alternatively, the silica may be preformed into the desired shape, e.g. pellets, spheres or the like, and the added base may be impregnated into the silica. Thus, any desired means of forming the catalyst may be employed.

A basic pyrogenic silica catalyst is required for the process of the present invention, since the base reacts with the acidic α-hydrogen atom on the methylene group in order to provide a carbanion for conversion to the unsaturated acid. Accordingly, any material, whether organic or inorganic which when dissolved in deionized water provides a pH of 3.0 or higher may be employed with the pyrogenic silica in order to provide the basic catalyst of the present invention. A pH of 3.0 is sufficiently basic for the purpose of the present invention because of the high acidity of the α-hydrogen atom on the alkanoic acid or its ester.

Thus, according to the preferred form of the catalyst of the present invention, the catalyst comprises between about 0.25 and about 5 mole percent by weight of an organic or inorganic base, preferably between about one and about 2 mole percent based upon the pyrogenic silica. Although pyrogenic silica provides an excellent catalyst for the process of the present invention, pyrogenic zirconia and pyrogenic titania are unsuitable, since their use results in an uncontrollable rise in temperature in the reaction zone and thereby causes excess gas to be produced. However, it has been found that the addition of between about one and about 10 percent by weight of pyrogenic zirconia in admixture with the pyrogenic silica of the present invention, provides an excellent catalyst. Likewise pyrogenic zirconia and titania may be produced by a synthesis route which is similar to that described above for pyrogenic silica, e.g., pyrogenic zirconia may be produced from zirconium tetrachloride.

Suitable reaction conditions for the reaction of the alkanoic acid or its ester with formaldehyde include the use of elevated temperatures. For example, suitable temperatures include, for example, between about 330° and about 390°C., preferably between about 340° and about 370°C. Atmospheric pressure is preferred, however, elevated pressures may be employed if desired. The concentration of reactants employed is varied over a range that is between about 0.3 and about 3 moles of alkanoic acid, an ester thereof or an alkyl nitrile per mole of formaldehyde. An especially preferred range is between about 0.8 and about 2 moles of acid, ester or nitrile per mole of formaldehyde. Likewise, the amounts of water and methyl alcohol present along with acid or ester and formaldehyde may be varied over a wide range. For example, the mole ratio of acid to formaldehyde to water to methanol is in the range of 1/1/0.01/0 to 1/1/6/0.03.

Likewise, the ratio of catalyst to feedstock may be varied over a broad range. A suitable flow rate which may be employed is, for example, a W/F (grams of catalyst/liter of feed/minute) of between about 100/0.2 and 100/10. A gaseous hourly space velocity in the range of between about 50 or 100 and about 2000 or 3000$^{-1}$, preferably in the range of between about 300 and about 600 GHSV may be utilized.

The present invention may be more fully understood from the following illustrative examples wherein the ratios and percentages are by weight and the temperatures are in degrees Centigrade unless otherwise specified.

EXAMPLE 1

A four-liter resin flask is charged with 2,500 milliliters of deionized water and 200 grams of a pyrogenic silica having a surface area of 136 square meters per gram, a total porosity of 10 cubic centimeters per gram and a macropore content (pores having a diameter greater than 100,000A) of 56 percent. Additional physical properties of the pyrogenic silica employed herein are given in Table I below, in connection with Catalyst A along with the properties of other pyrogenic silicas that are employed in examples hereafter presented:

Table I

| Catalyst | Surface Area ($m^2/g$) | Pore Size Distribution ($A° \times 1000$) | | | Total Porosity (cc/g) |
|---|---|---|---|---|---|
| | | >100 | 100–10 | 10–1 | <1 | |
| A | 136 | 56 | 21 | 13 | 11 | 10 |
| B | 400 | 31 | 40 | 20 | 9.2 | 7.8 |
| C | 117 | 38 | 45 | 12 | 5.2 | 8.8 |
| D[1] | 150 | 48 | 27 | 14 | 11 | 12 |

[1]Silica structure modified with 16 percent alumina

The mixture is slurried at room temperature, and 2.45 grams of 85.5 percent potassium hydroxide in 90 milliliters of deionized water are added. The slurry is agitated and heated until a thick paste is formed. The paste is dried at a temperature of 120°C. overnight and calcined for 8 hours in air at a temperature of 380° to 385°C. in a sealed muffle furnace. The resulting material is then sieved to provide a catalyst having a 6 to 20 mesh particle size.

EXAMPLE 2

The catalyst of Example 1 in an amount of 123 grams is charged to a 1 inch by 32 inch tubular reactor that is equipped with a preheater. The reactor is heated to a temperature of 370°C., while a feedstream having propionic acid to formaldehyde to water to methyl alcohol mole ratio of 20/20/59/1 is fed to the reactor. The ratio of the catalyst (in grams) to the total gas flow (liters per minute) or W/F factor is 100/1.

The conversion to monomer (methacrylic acid and methyl methacrylate) based on formaldehyde and propionic acid fed, is 34 percent, while the yield of monomer is about 62 percent, based upon the formaldehyde consumed and about 71 percent based upon the propionic acid that is consumed. The formaldehyde accountability, i.e., the percentage either recovered as such (and hence recyclable) or converted to monomer is about 79 percent. The corresponding value for propionic acid is about 87 percent.

The following equations illustrate the manner in which percent conversion, yield and accountability are calculated for the purpose of this and other Examples:
Conversion of Formaldehyde to Monomer:

$$\text{Percent conversion} = \frac{\text{moles of MA and MM recovered}}{\text{moles F fed to reactor}}$$

where
Ma = methacrylic acid
MM = methyl methacrylate
F = formaldehyde
Conversion of Propionic Acid to Monomer:

$$\text{Percent conversion} = \frac{\text{moles of MA and MM recovered}}{\text{moles PA fed to reactor}} \times 100$$

where PA = propionic acid
Yield of Monomer Based on Formaldehyde:

$$\text{Percent yield} = \frac{\text{moles of MA and MM recovered}}{\text{moles F converted}} \times 100$$

Yield of Monomer Based on Propionic Acid:

$$\text{Percent yield} = \frac{\text{moles of MA and MM recovered}}{\text{moles PA converted}} \times 100$$

Accountability of Formaldehyde:

$$\text{Percent accountability} = \frac{\text{moles of F, MA and MM recovered}}{\text{moles F fed}} \times 100$$

Accountability of Propionic Acid:

$$\text{Percent account ability} = \frac{\text{moles of PA, MP, MA and MM recovered}}{\text{moles PA fed}} \times 100$$

where MP = methyl propionate

EXAMPLE 3

For comparative purposes, a silica gel catalyst is provided with potassium hydroxide in the manner described in Example 1. Thus, 2.45 grams of 85.5 percent potassium hydroxide are dissolved in 90 milliliters of deionized water and are added to 200 grams of silica gel, having the properties shown in Table II, below, in connection with Catalyst E:

Table II

| Support | Surface Area (m²/g) | Pore Size Distribution (A° × 1000) | | | | Total Porosity (cc/g) |
|---|---|---|---|---|---|---|
| | | 100 | 100-10 | 10-1 | 1 | |
| E[1] | 447 | 7.7 | 77 | 13 | 2.5 | 0.68 |
| F[1] | 675 | 0 | 0 | 100 | 0 | 0.02 |
| G[1] | 542 | 25 | 75 | 0 | 0 | 0.08 |
| H[2] | 95.7 | | 15 | 66 | 11 | 2.17 |
| I[3] | 113 | | 0 | 17 | 67 | 0.09 |

[1]Commercial silica gels.
[2]Laboratory synthesized catalyst that is prepared as a precipitate by adding HCl to a sodium silicate solution.
[3]Sodium aluminosilicate.

After the potassium hydroxide is added to the silica gel, the resulting solid is dried and calcined for 8 hours at a temperature of 363°–383°C.

The resulting catalyst having a particle size of 6–20 mesh is employed in the reactor of Example 2 with the feed and conditions of Example 2. Employing the silica gel catalyst, only 28 percent of the reactants are converted to monomer. The yield based upon formaldehyde is about 58 percent and the yield based upon propionic acid is about 58 percent as well. The formaldehyde and propionic acid accountabilities are 80 and about 82 percent, respectively.

EXAMPLE 4

For further comparative purposes, a sodium aluminosilicate catalyst is provided with one percent potassium hydroxide in the manner described for the pyrogenic silica of Example 1. Thus, 2.5 grams of 86.5 percent potassium hydroxide, dissolved in 150 milliliters of deionized water are added to 200 grams of sodium aluminosilicate, which has the properties specified for Catalyst I in Table II, i.e., a surface area of 113 square meters per gram and a total porosity of 0.09 cc. per gram. The mixture is dried and calcined for 8 hours at a temperature of 383°C.

Formaldehyde, propionic acid, water and methanol are fed to the tubular reactor in the amounts and under the conditions described in Example 2. The resulting conversion is 8.7 percent, while the yield based upon formaldehyde and propionic acid are 23 and 27 percent, respectively. The formaldehyde and propionic acid accountabilities are 71 and 79 percent, respectively.

As shown in Table III, below, the pyrogenic silica not only produces higher conversions of feed to monomer (methacrylic acid and methyl methacrylate), but also provides higher yields and accountabilities.

Table III

| Example No. | Catalyst | Conversion To Monomer (Percent) | Yield of Monomer (Percent) | | Accountability (Percent) | |
|---|---|---|---|---|---|---|
| | | | Based Upon Acid | Based Upon Formaldehyde | Based Upon Acid | Based Upon Formaldehyde |
| 2 | KOH/pyrogenic silica | 34 | 71 | 62 | 88 | 79 |
| 3 | KOH/silica gel | 28 | 58 | 58 | 82 | 80 |
| 4 | KOH/sodium aluminosilicate | 8.7 | 27 | 23 | 79 | 71 |

EXAMPLES 5–7

The procedure of Example 2 is repeated employing the other pyrogenic silica Catalysts B, C and D whose properties are indicated in Table I. Thus, propionic acid and formaldehyde are reacted at a temperature of 370°C. employing each of the Catalysts B, C and D of Table I wherein each catalyst contains one percent potassium hydroxide, which has been provided to the catalyst in the manner described in Example 1. The results are shown in Table IV, below.

Table IV

| Example No. | Reactor Temperature (°C.) | Conversion To Monomer (Percent) | Yield of Monomer (Percent) | | Accountability (Percent) | |
|---|---|---|---|---|---|---|
| | | | Based Upon Acid | Based Upon Formaldehyde | Based Upon Acid | Based Upon Formaldehyde |
| C | 370 | 30 | 66 | 61 | 86 | 81 |
| B | 370 | 33 | 65 | 55 | 84 | 73 |
| D[1] | 370 | 8.4 | 25 | 13 | 81 | 45 |

[1]Contains 16 percent alumina.

As can be seen upon viewing Table IV, a high conversion, yield and accountability are provided employing the pyrogenic silica Catalyst B and C. However, pyrogenic silica Catalyst D, which contains 16 percent alumina, results in lower conversion, yield and accountability.

EXAMPLES 8-10

The procedure of Example 2 is repeated employing the silica Catalysts F, G and H having the properties indicated in Table II. Thus, the silica gel Catalysts F and G and the precipitated silica Catalyst H, each of whose physical properties are set forth in Table II, are provided with one percent potassium hydroxide in the manner described for the pyrogenic silica of Example 1 and are employed for the reaction of propionic acid and formaldehyde in the manner described in Example 2. The results are set forth in Table V, below:

Table V

| Example No. | Catalyst | Conversion To Monomer (Percent) | Yield of Monomer (Percent) | | Accountability (Percent) | |
|---|---|---|---|---|---|---|
| | | | Based Upon Acid | Based Upon Formaldehyde | Based Upon Acid | Based Upon Formaldehyde |
| 8 | F | 25 | 49 | 43 | 75 | 67 |
| 9 | G | 29 | 63 | 50 | 83 | 71 |
| 10 | H[1] | 28 | 75 | 54 | 91 | 76 |

[1] Synthesized by acid precipitation from sodium metasilicate solution

As seen upon viewing Table V, the conversions and yields are well below that achieved with the pyrogenic silica of the previous Examples.

EXAMPLES 11-20

A number of diverse catalysts employing a wide variety of supports and carrying one percent potassium hydroxide are synthesized and evaluated in the process of Example 2. The results are shown in Table VI, below:

Table VI

| Example No. | Catalyst | Reactor Temperature (°C) | Conversion To Monomer (Percent) | Yield of Monomer (Percent) | | Accountability (Percent) | |
|---|---|---|---|---|---|---|---|
| | | | | Based Upon Acid | Based Upon Formaldehyde | Based Upon Acid | Based Upon Formaldehyde |
| 11 | Pyrogenic Silica | 370 | 34 | 71 | 62 | 88 | 79 |
| 12 | Glass Balloons | 355 | 3.1 | 8.4 | 7.5 | 66 | 61 |
| 13 | Ceramic Silica | 385 | 5.2 | 33 | 22 | 89 | 81 |
| 14 | Allundum | 385 | 3.5 | 100 | 21 | 100 | 86 |
| 15 | Silica Gel | 370 | 28 | 58 | 59 | 82 | 80 |
| 16 | Sodium Aluminosilicate | 355 | 9.2 | 47 | 29 | 92 | 77 |
| 17 | Glass Microbeads | 370 | 8.9 | 52 | 42 | 92 | 88 |
| 18 | Alumina | 385 | 17 | 35 | 24 | 73 | 46 |
| 19 | Silica Sol | 355 | 21 | 50 | 43 | 80 | 72 |
| 20 | Microcrystalline Silica | 385 | 3.4 | 9 | 5.4 | 65 | 41 |

As can be seen upon viewing Table VI, all of the catalysts tested are inferior to the pyrogenic silica catalyst of Example 11.

EXAMPLE 21

A buffered cesium hydroxide catalyst composition is prepared by adding a solution containing 4.5 grams of cesium hydroxide, 0.05 gram of disodium hydrogen phosphate, 0.09 gram of borax and 100 milliliters of water, to a stirred suspension of 156 grams of pyrogenic silica in 1850 milliliters of deionized water.

The resulting composition is stripped while stirring to remove solvent, dried and calcined for 8 hours at a temperature of 383°C.

The resulting catalyst is employed for the conversion of propionic acid and formaldehyde in the manner described in Example 2. A conversion of 34 percent is achieved at a temperature of 370°C., while yields based upon formaldehyde and propionic acid are 69 and 80 percent, respectively. The formaldehyde accountability is 85 percent, while the propionic acid accountability is 93 percent.

EXAMPLE 22

The pyrogenic silica catalyst described in Example 1 is heated to a temperature of 355°C. Meanwhile, a feedstream comprising 20 mole percent formaldehyde, 20 mole percent acetic acid, 59 mole percent water and 1 mole percent methanol is passed over the pyrogenic silica catalyst bed at a W/F factor of 100 to 1 grams per liter per minute.

Conversion to monomer (acrylic acid and methyl acrylate) is 12 percent, while yields based upon formaldehyde and acetic acid are 46 and 72 percent, respectively. The formaldehyde and acetic acid accountabilities are 86 and 95 percent, respectively.

EXAMPLE 23

A pyrogenic silica catalyst containing about 6 percent by weight zirconia is employed in the reactor described in Example 2 with the feedstock and conditions utilized therein, with the exception that a lower conversion temperature of 340°C. is used.

A conversion of 25 percent is achieved.

EXAMPLE 24

The procedure of Example 2 is repeated with the exception that methyl propionate is substituted for propionic acid.

The conversion is 25 percent, while the combined yields of monomer (MAA + MMA) based on formaldehyde and methyl propionate are 63 percent and 44 percent, respectively, while another 40 percent of the methyl propionate goes to propionic acid. The formaldehyde accountability is 85 percent, while that for methyl propionate is 91 percent.

EXAMPLE 25

The procedure of Example 2 is repeated with the exception that acetonitrile is substituted for propionic acid. The conversion is 6.5 percent while the yield of acrylonitrile based on formaldehyde and on acetonitrile, respectively is 15 percent. The formaldehyde and acetonitrile accountabilities are 65 and 64 percent, respectively.

EXAMPLE 26

In the following examples, pyrogenic silicas that have been treated with a variety of materials and then calcined in the manner described in Example 1, are evaluated employing the feedstream, reactor and conditions set forth in Example 2. The results of this evaluation are given in Table VII, below. All of the cesium-containing catalysts have been buffered with disodium phosphate and sodium tetraborate in the manner described in Example 21.

TABLE VII

| Ex. No. | Catalyst | Catalyst Concentration (mole % actives/ support) | Reactor Temp. (°C.) | W/F (g./cat./ l./min.) | Conversion To Monomer (%) | Yield of Monomer (%) | | Accountability (%) | |
|---|---|---|---|---|---|---|---|---|---|
| | | | | | | On Acid | On CH$_2$O | On Acid | On CH$_2$O |
| 26 | CsOH | 1.3 | 370 | 100/1 | 31 | 54 | 43 | 74 | 59 |
| | Cs stearate | 0.8 | | | | | | | |
| 27 | Cs stearate | 0.8 | 425 | 100/7 | 17 | 30 | 25 | 64 | 53 |
| 28 | CsOH | 5 | 370 | 100/1 | 20 | 40 | 33 | 71 | 58 |
| 29 | CsOH | .3 | 370 | 100/1 | 19 | 73 | 50 | 82 | 95 |
| 30 | (CH$_3$)$_4$NOH | 1.1 | 370 | 100/1 | 7.0 | 99 | 44 | 99 | 91 |
| 31 | Na$_4$P$_2$O$_7$.10H$_2$O | 1.5 | 370 | 100/1 | 13 | 50 | 30 | 91 | 76 |
| 32 | (CH$_3$(CH$_2$)$_7$)$_4$NOH | 6 | 385 | 100/1 | 6.8 | 30 | 27 | 85 | 82 |

Although the invention has been described in considerable detail with particular reference to certain preferred embodiments thereof, variations and modifications can be effected within the spirit and scope of the invention as described hereinbefore, and as defined in the appended claims.

What is claimed is:

1. A process for the production of α,β-ethylenically unsaturated acids, esters of said acids having 4 to 15 carbon atoms and nitriles which comprises reacting formaldehyde with an alkanoic acid, an ester of said acid having 3 to 14 carbon atoms, or an alkyl nitrile in the presence of a catalyst consisting of pyrogenic silica, with a total surface area of 150 to 300 square meters per gram, a total porosity volume of 3 to 15 cubic centimeters per gram and a pore size distribution such that pores having a diameter in excess of 100,000 A. and pores between 100,000 and 10,000 A. total at least 50% of the total pore content and less than 30% total pore content is of pores having a diameter of less than 1,000 A., with the remainder of pores in the range of 10,000 to 1,000 A., calcined with a base activating agent and where the reaction is carried out at a temperature of 330° to 390°C. with an alkanoic acid, ester or alkyl nitrile to formaldehyde molar concentration in the range of about 0.3–3.0:1.

2. The process of claim 1 wherein alkanoic acids are reacted with formaldehyde and said acids contain between 2 and 9 carbon atoms per molecule.

3. The process of claim 2 wherein said alkanoic acid is propionic acid.

4. The process of claim 1, wherein said catalyst contains as a base activating agent a compound selected from the group consisting of hydroxides, oxides, superoxides, or amides and salts of a metal of Group IA, IIA or IIIB.

5. The process of claim 4 wherein said base activating agent is an alkali metal hydroxide.

6. The process of claim 5 wherein said alkali metal hydroxide is potassium hydroxide or cesium hydroxide.

7. The process of claim 1 wherein said pyrogenic silica has a total porosity of between about 6 and about 10 cubic centimeters per gram.

8. The process of claim 1 wherein said ester is methyl propionate.

9. The process of claim 1 wherein alkyl nitriles containing two to about nine carbon atoms per molecule are reacted with formaldehyde.

10. The process of claim 9 wherein said alkyl nitrile is propionitrile.

11. The process of claim 1 wherein said process is conducted at a temperature in the range of between about 340° and about 370°C.

12. The process of claim 1 wherein between about one and about 10 percent by weight of zirconia is admixed with said pyrogenic silica.

* * * * *

UNITED STATES PATENT AND TRADEMARK OFFICE
CERTIFICATE OF CORRECTION

PATENT NO. : 3,933,888
DATED : January 20, 1976
INVENTOR(S) : Francis W. Schlaefer It is certified that error appears in the above-identified patent and that said Letters Patent are hereby corrected as shown below:

Column 11, line 3, the heading "EXAMPLE 26" should read -- EXAMPLES 26-32 --.

Columns 11-12, Table VII, the formulae under Catalyst (2nd) column:

For Ex. 30:

" $(CH_2)_4NOH$ " should read -- $(CH_3)_4NOH$ --

For Ex. 32:

" $(CH_2(CH_2)_7)_4NOH$ " should read -- $(CH_3(CH_2)_3)_4NOH$ --

Signed and Sealed this

Eighteenth Day of October 1977

[SEAL]

Attest:

RUTH C. MASON
*Attesting Officer*

LUTRELLE F. PARKER
*Acting Commissioner of Patents and Trademarks*